(12) United States Patent
Johnson et al.

(10) Patent No.: US 7,088,434 B2
(45) Date of Patent: Aug. 8, 2006

(54) APPARATUS AND METHOD FOR PROVIDING SPOT LIGHTING FOR GEMSTONE OBSERVATION

(75) Inventors: Mary L. Johnson, San Diego, CA (US); Alvan Gilbertson, Murrieta, CA (US); David Rosenthal, Seal Beach, CA (US)

(73) Assignee: Gemological Institute of America, Inc., Carlsbad, CA (US)

( * ) Notice: Subject to any disclaimer, the term of this patent is extended or adjusted under 35 U.S.C. 154(b) by 0 days.

(21) Appl. No.: 10/641,386

(22) Filed: Aug. 13, 2003

(65) Prior Publication Data
US 2005/0036131 A1   Feb. 17, 2005

(51) Int. Cl.
*G01N 21/00* (2006.01)
(52) U.S. Cl. .................................................. 356/30
(58) Field of Classification Search ................ 356/30
See application file for complete search history.

(56) References Cited

U.S. PATENT DOCUMENTS 3,751,162 A * 8/1973 Long ........................... 356/30
3,989,379 A * 11/1976 Eickhorst ..................... 356/30
4,906,083 A * 3/1990 Sattler ......................... 359/386
5,811,817 A * 9/1998 Ravich ........................ 250/372
6,473,164 B1 * 10/2002 De Jong et al. ............... 356/30

OTHER PUBLICATIONS

T. Scott Hemphill, Modeling the Appearance of the Round Brilliant Cut Diamond: An Analysis of Fire of Brilliance, Fall 1998, Gems & Gemology, pp. 158-183.
Irene M. Reinitz, Modeling the Appearance of the Round Brilliant Cut Diamond: An Analysis of Fire, and More about Brilliance, Fall 2001, Gems & Gemology, pp. 174-197.

* cited by examiner

*Primary Examiner*—Gregory J. Toatley, Jr.
*Assistant Examiner*—Roy M. Punnoose
(74) *Attorney, Agent, or Firm*—DLA Piper Rudnick Gray Cary US LLP; Andrew V. Smith

(57) ABSTRACT

An apparatus, system and method for providing spot lighting for observing a gemstone is presented. In particular, the spot lighting provided by the invention allows for observing of the fire of a gemstone, i.e. the visible effects of light dispersion into separate colors. The apparatus includes a tube for receiving a portion of a multi-spectral light source, and a mask coupled to the tube for blocking other portions of the light source. By selecting the proper tube dimensions and aligning the tube with both the light source at an inlet and a gemstone at an outlet, the spot lighting source provides direct lighting for isolating and accentuating the effects of fire.

19 Claims, 3 Drawing Sheets

APPARATUS AND METHOD FOR PROVIDING SPOT LIGHTING FOR GEMSTONE OBSERVATION

BACKGROUND OF THE INVENTION

The present invention generally relates to gemstone observation, and more particularly to an apparatus and method for isolating and observing the fire of a gemstone.

The quality and value of faceted gemstones are often described in terms of the "four C's": carat weight, color, clarity and cut. Carat weight is the most objective, because it is measured directly on a balance. Color and clarity are factors for which grading standards have been established by the Gemological Institute of America (GIA), among others.

Cut is much less tractable. Unlike color and clarity, for which a legacy of teaching, trading, and laboratory practice have created a general consensus, there are a number of different grading systems for grading cut of a gemstone. Inherent in most of these systems is the premise that there is one set, or a narrow range, of preferred proportions for some gemstones, and that any deviation from this set of proportions diminishes the appearance or attractiveness of the gemstone. However, under this premise, gemstone cutters typically apply these proportions only to obtain the largest possible size gemstone from an uncut stone, without specific regard to the stone's eventual appearance.

Most gemstones are a convex polyhedron which can be specified according to a number of parameters. FIG. 1 illustrates various parameters that define the proportions of one type of gemstone, a round brilliant cut (RBC) diamond. This type of gemstone can be specified according to eight parameters. Crown angle is the angle, in degrees, between the bezel facets and the girdle plane. Pavilion angle is the angle, in degrees, between the pavilion mains and the girdle plane. Table size represents the width of the table as a percent of the girdle diameter. Culet size represents the width of the culet as a percent of the girdle diameter. Star length is a ratio of the length of the star facets to the distance between the table edge and girdle edge. Lower girdle length represent a ratio of the length of the lower girdle facets to the distance between the center of the culet and the girdle edge. Girdle thickness is preferably measured between bezel and pavilion main facets, and is expressed as a percentage of girdle diameter. Finally, girdle facet number is the total number of facets on the girdle. Given a number of gemstones of the same color, weight and clarity, varying any of the above parameters produce different appearances.

Other than color, weight, and clarity, gemstone appearance has historically been described chiefly in terms of three aspects: brilliance, scintillation, and fire. While interrelated, these aspects can be characterized independently. Brilliance, or brightness, generally refers to the level of white light returned through the crown of a gemstone to an observer overhead. Scintillation refers to flashes of light reflected from the crown of a gemstone, particularly as the gemstone is rotated or tilted. Fire is the result of the light-dispersive quality of a gemstone, and refers to visible rays or flares of colored light returned by the gemstone.

It is believed that with knowledge about how cut relates to each of these aspects, alone or in combination, then perhaps improved cut parameters can be established to yield more attractive, and thus more valuable, gemstones. Unfortunately, each aspect above represents a complex concept without a precise mathematical definition, making it very difficult to measure on actual gemstones.

Models have been developed for some aspects, however. For example, GIA developed a mathematical model for brilliance, discussed in *Modeling the Appearance of the Round Brilliant Cut Diamond: An Analysis of Brilliance*, by Hemphill et al., Gems & Gemology, Vol. 34, No. 3, pp. 158–183, the contents of which are incorporated by reference herein in their entirety and for all purposes. GIA's brilliance model uses a simulated round brilliant cut (RBC) diamond and a modeled light source of diffused, hemispherical white light shining on the crown. Then, researchers used computer simulation techniques to examine mathematically how millions of rays of light from the virtual light source interact with the virtual gemstone. This model generated images and a numerical measurement of the optical efficiencies of the gemstone called weighted light return (WLR). The WLR is a weighted sum of the amount of light returned through the crown of the virtual diamond to all positions of observation above the girdle. Thus, WLR approximates overall brilliance in an environment with even diffused lighting and no objects, such as an observer, in the environment.

Similar assumptions and qualifications were used in developing a metric for fire. See *Modeling the Appearance of the Round Brilliant Cut Diamond: An Analysis of Fire, and More About Brilliance*, Gems & Gemology, Vol. 37, No. 3, pp. 174–197, the contents of which are also incorporated by reference herein for all purposes. While brilliance is emphasized with diffuse illumination found in most common lighting environments, fire is best observed using a highly directed, narrow beam of light, referred to herein as "spot lighting." Accordingly, GIA chose to model the directed lighting as a bright point source of illumination located very far from the gemstone, i.e. at infinite distance, centered over and directed toward the gemstone's table. Under these conditions, the unpolarized light rays entering the crown facets are parallel to one another and perpendicular to the table, to illuminate the entire crown. The metric derived—dispersed colored light return, or DCLR—describes the potential of an RBC gemstone with certain proportions to display dispersed colored light when viewed face-up.

Fire is the most difficult aspect of a gemstone to observe. Fire is often mixed with scintillation, the white light flashes that obscure the rays of colored light. Further, white light in general, either from the lighting environment itself or returned from the gemstone as brilliance, can overwhelm and suppress the visible effects of fire.

A particular type of directed light source, for example one which approximates the GIA modeled light source, can isolate or enhance observable fire. However, several problems exist with finding and using such a source. Commercially-available narrow beam spot lights are not sufficiently directed, and allow too much white light from too many angles to reach a gemstone being observed, obscuring the fire. On the other hand, some highly directed light sources, such as lasers or light emitting diodes, radiate at too little of the visible spectrum for viewing the full range fire-based color separation. What is needed is a apparatus and method by which a white light source is channeled directly to a gemstone, in order to better isolate, observe and measure fire.

SUMMARY OF THE INVENTION

The present invention is directed toward providing a light source which isolates and accentuates a gemstone's fire. This invention overcomes the limitations of conventional lighting schemes by providing directed, spot lighting having a full spectrum of visible radiant energy, which allows an observer to view the full extent of dispersion of light within a gemstone into separate wavelengths.

In one exemplary embodiment of the invention, an apparatus for providing a spot lighting source for observing fire of a gemstone includes a tube. The tube has an inlet for receiving a portion of light from a light source, and an outlet for providing spot lighting from the received portion of light channeled through the tube. Accordingly, the spot lighting carries approximately the same spectrum as the original light source. The apparatus further includes a mask, coupled with the tube to shield the outlet from other portions of light from the light source.

The another embodiment, a method of observing fire from a gemstone includes the steps of receiving a portion light from a visible or white light source at an inlet of a tube, and channeling the received portion of light through the tube. The method further includes the step of outputting the channeled light as spot lighting from an outlet of the tube. In the embodiment, the light channeled through the tube is directed but not diminished, so that the spot lighting has approximately the same spectrum as the light from the light source.

DETAILED DESCRIPTION OF THE PREFERRED EMBODIMENTS

This invention relates to an apparatus and method for isolating colored light returned from within a gemstone. More specifically, this invention provides an apparatus and method for providing directed or spot lighting to a gemstone for observing the full effects of dispersion of a white light source by the gemstone into individual rays of colored light, known as "fire." In a particular embodiment, this invention uses a conventional daylight-approximating light source and provides narrow spot lighting having the same or near-same spectral characteristics as the light source. Thus, this invention avoids the need for lenses, internal reflective layers for light propagation, or other mechanisms that modify or alter a light source.

Figure 1:
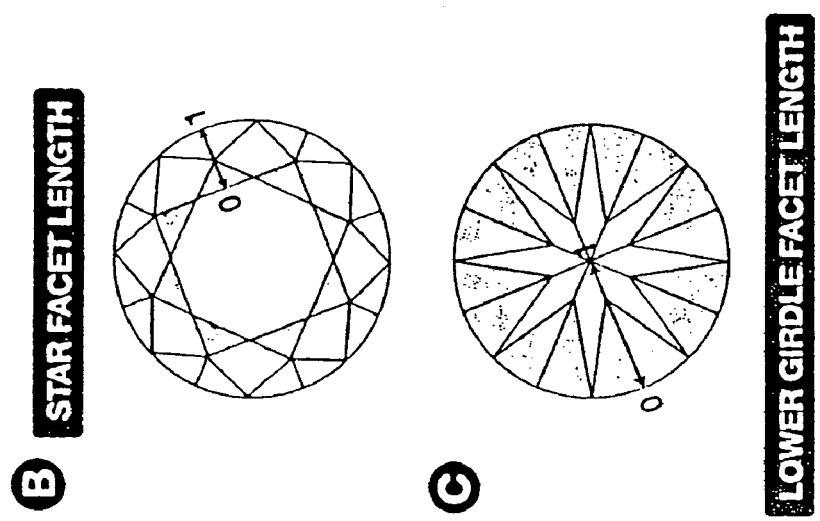
FIG. 1 illustrates various proportions of one type of gemstone.
Figure 1:
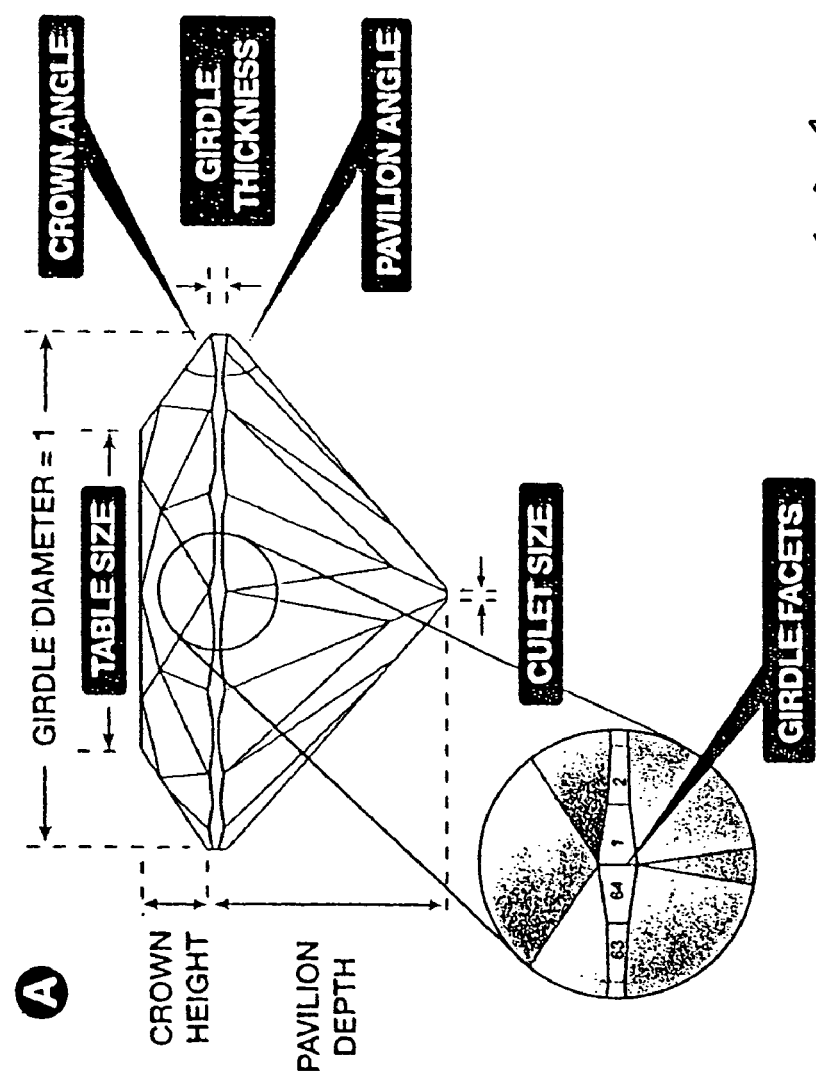
Figure 2:
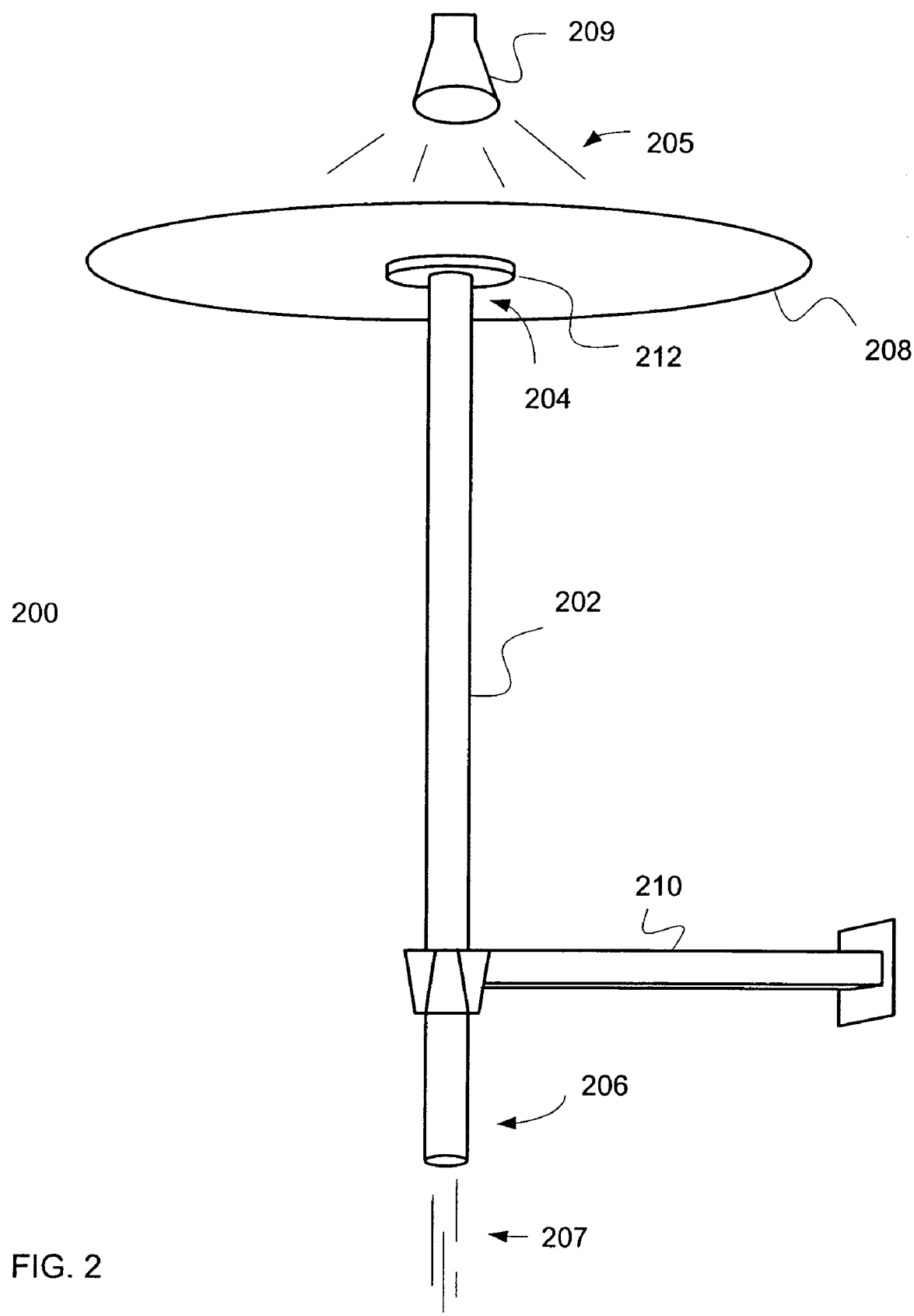
FIG. 2 is a perspective view of a system for providing a spot light source for observing fire of a gemstone.

FIG. 2 shows an embodiment of an apparatus 200 for providing spot lighting to a gemstone. The apparatus 200 is generally adapted for use with any light source, but is preferably employed in combination with a daylight-approximating light source. As used herein, "daylight approximating" refers to a light source that approximates diffused, white light, or in other words, light which radiates all or nearly all of the visible electromagnetic radiation spectrum. The preferred operating environment for the apparatus 200 is dark other than the light source described herein.

The apparatus includes a tube 202. The tube includes an inlet 204 and an outlet 206 on an opposite end from the inlet 204. The inlet 204 is configured to receive a portion of light 205 from a light source 209, which received light is channeled through the tube 202 toward the outlet 206. The portion of light 205 received at the inlet 204 can represent, for example, 1 to 5 degrees in arc-length of a cross-section of the radiation profile of light 205 emitted from the light source 209. The apparatus 202 also includes a mask 208 coupled to the tube 202 to shield other portions of the light 205 from the tube 202 or outlet 206.

The tube 202 is preferably straight, elongate and hollow. In an alternative embodiment, the tube 202 may have a squared or angled cross-section along its circumference. The tube 202 is preferably 0.5 to 6 feet in length, and in a specific embodiment is 2 to 3 feet in length. The tube 202 may be any length, however, that sufficiently channels light without excessive loss. The interior diameter of the tube 202 is preferably between 0.1 and 1 inches. In one exemplary embodiment, the tube 202 has an inner diameter of approximately 0.5 inches. In yet another embodiment, the apparatus 200 can include, inside tube 202 or near the inlet 204 or outlet 206, an aperture or an iris that is adjustably sized for different-sized gemstones.

The tube 202 can be formed of metal, plastic or glass, or any other suitably rigid material, such as ceramic or polypropylene. The tube 202 is formed of a material having an inner polished surface that channels light with a particular amount of reflection, absorption, or dispersion, and preferably minimizing each. In one embodiment, the tube 202 includes an interior coating or layer that is selected for its particular light propagation qualities.

In a preferred embodiment, the apparatus 200 is used in combination with a light source 209 that is a daylight-approximating halogen lamp, such as an MR16 halogen display lamp (12 Volt, 50 Watt, 4700K color temperature and 10 degree narrow spot) manufactured by Solux™. The light source 209 can include a filter. While white light is preferred, it should be understood that other types of light-producing devices may suitably be used as the light source 209.

The mask 208 is preferably coupled to the tube 202 at or near the inlet 204, but is generally positioned between the inlet 204 and the outlet 206. In one embodiment of the invention, the mask 208 is shaped to correspond to the illumination profile or pattern of the light source 209. For example, the mask 208 can be round and rigid like a plate. However, it should be readily apparent to one skilled in the art that the mask 208 can have any shape, and a wide range of sizes and rigidity. The mask 208 is also preferably planar and thin, but can have any thickness. The mask 208 can be formed of any rigid or semi-rigid, sufficiently opaque material or structure which can block the passage of light radiation emitted from the light source 209 or other extraneous sources of light in the lighting environment. In this regard, the exterior surface of the mask 208 and the outer surface of the tube 202 can be dark and non-reflective in a practical implementation to reduce the amount of potential light reflections. Additionally, the mask 208 should be resistant to any thermal radiation generated by the light source 209.

The apparatus 200 can also include a mounting mechanism 210 for mounting the tube 202 to a fixed object, and for positioning the tube 202 at a particular orientation or location. For instance, the mounting mechanism 210 can have one end configured to attach to a wall, or to mount to a table or other flat surface. The other end of the mounting mechanism 210 can be coupled to the tube 202. The mounting mechanism 210 is used to align the inlet 204 of the tube 202 with the light source 209, and/or align and adjust the height or position of the outlet 206 relative to a gemstone being observed. In another embodiment, the tube 202 is held stationary by the mounting mechanism 210, and a gemstone being observed is positioned a suitable distance away from the outlet 206 of the tube. In accordance with one practical embodiment, the gemstone is held at least three feet away from the outlet 206.

Figure 3:
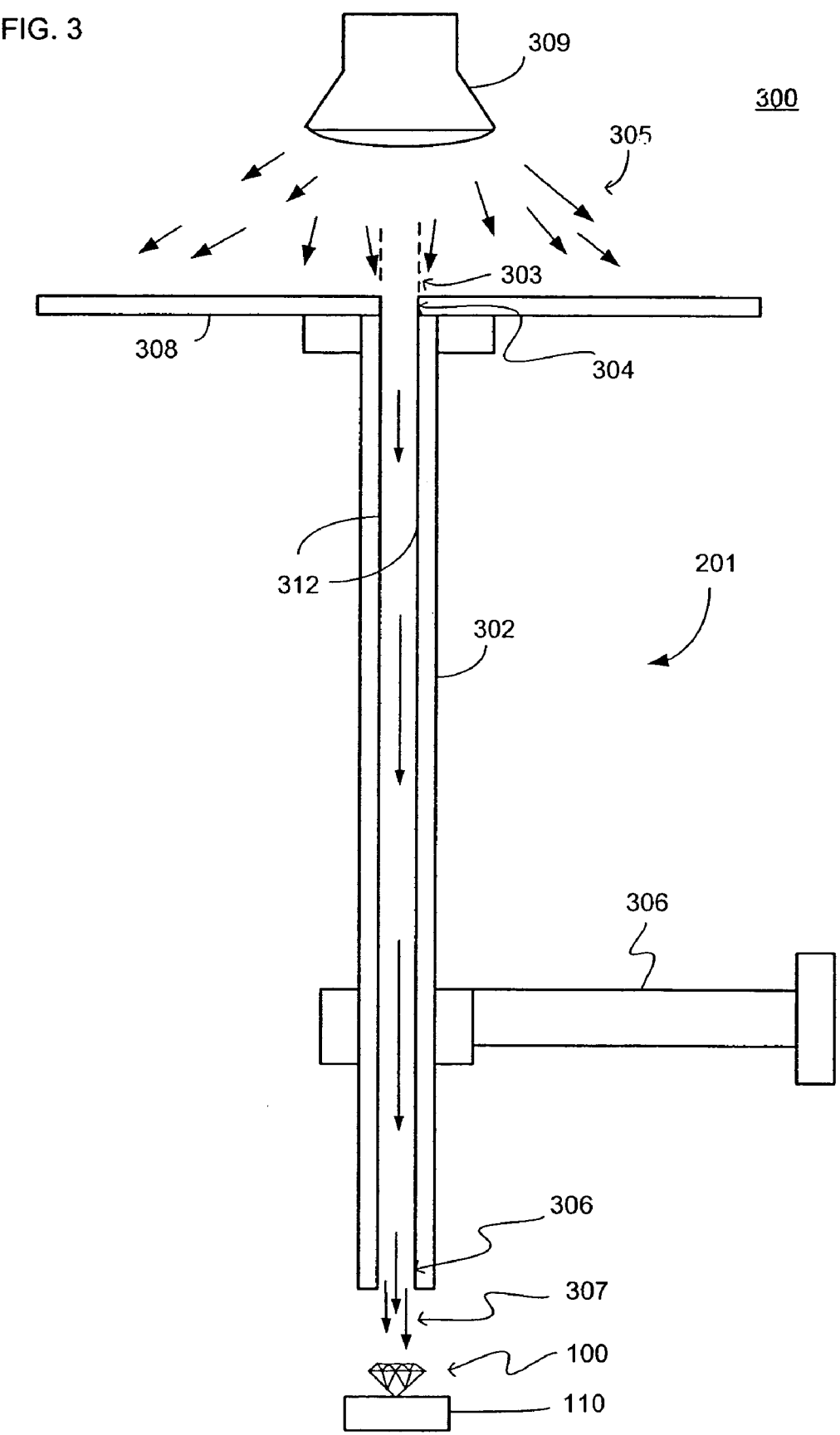
FIG. 3 is a cross-sectional view of a system for providing a spot light source from a portion of light from a light source to a gemstone.

FIG. 3 is a cross-sectional view of an apparatus 201 for providing spot lighting, employed in a system 300 for observing fire of a gemstone 100. Along with the apparatus 201, the system 300 also includes a stage 110 for supporting one or more gemstones 100 being observed. The stage 110 is shown supporting only one gemstone for simplicity, however the stage 110 may be configured to support two or more gemstones. The stage 110 is preferably non-reflective. In one embodiment, the stage 110 is configured for supporting the gemstone 100 in a table-up position to allow for the maximum amount of dispersed colored light to be returned through the crown.

When gemstone 100 is near, i.e. directly under, the outlet 306 of the tube 302, and the light source 309 is near, i.e. directly over, the inlet 304 of the tube 302, a portion 303 of the light 305 emitted from the light source 309 is channeled through the interior 312 of the tube 302 in the direction indicated. The interior 312 is generally defined by a the cross-sectional inner area of the tube 302, summed along the length of the tube. The portion 303 of the light 305 generally corresponds to the area of the inlet 304, and includes visible radiation from any angle. The portion 303 of light 305 that is received at the inlet is channeled to the outlet 306, where it is provided as a directed, spot lighting 307. Importantly, very little to none of the visible spectrum of the received portion 303 of light is lost in the spot lighting 307.

A mask 308 shields an area around the gemstone from the light 305 of the light source 309. The mask 308 may also be configured to shield the area from other light of the lighting environment, such as indirect sunlight, other overhead lights, etc. The mask 308 therefore prevents dispersed white light from reaching the gemstone 100 and obscuring the effects of fire from the spot lighting 307.

In one embodiment, the apparatus 201 is stationary, and the stage 110 and light source 309 are moved to their positions. In an alternative embodiment, the stage 110 and light source 309 are stationary, and a mounting mechanism 310 is configured for allowing the tube 302 to be placed into position. In still yet another embodiment, the light source 309, the apparatus 201 and the stage 110 are all movable.

The present invention may be specifically embodied as a tool to train observers to look for the specific colored flashes or rays of light that emanate from a gemstone as a result of its dispersive qualities. This invention may also be embodied as a system for measuring or characterizing the effects of fire. In a measuring system, a measuring device such as a colorimeter may be positioned near the gemstone to determine and/or quantify the specific colors of the gemstone's fire. Alternatively, a photodetector or similar instrument may be used to determine a level of colored light returned by a gemstone, or compared with the spot lighting supplied by the apparatus 100. In this alternative embodiment, a filter or group of filters associated with the photodetector may be used to isolate specific wavelengths of visible colored light. A measuring system can also include a computer for processing measurement data, and a database for storing the results of the processing. Further, the database can be compiled as a reference, which can be accessed for later measurements and/or comparisons.

By isolating and observing the effects of fire of many gemstones, it can be determined how a particular cut relates to this aspect of a gemstone's appearance, assuming other factors such as color, clarity and weight are the same. Thus, this invention provides useful information for establishing a set of preferred proportions for gemstones.

While various embodiments of the invention are described above, it should be understood that they are presented for example only, and not as limitations to the following claims. Accordingly, the scope and breadth of the present invention should only be defined in accordance with the following claims and their equivalents.

What is claimed is:

1. An apparatus for transforming a wide-angle light source into a spot lighting source for observing the fire of a gemstone, comprising:
   a hollow tube having an inlet for receiving a portion of light from a said wide-angle light source disposed proximate to said inlet and an outlet for providing spot lighting from the light portion channeled through the tube, the spot lighting having approximately the same spectrum as the light from the light source; and
   a mask, coupled with the tube to shield light generated from the wide angle light source, other than the channeled light portion, from being incident upon the gemstone.

2. The apparatus of claim 1, further comprising a mounting mechanism, coupled to the tube between the inlet and outlet, for mounting and positioning the tube.

3. The apparatus of claim 1, wherein the mask is a plate coupled to the tube near the inlet.

4. The apparatus of claim 1, wherein the tube has a length of 0.5 to 6 feet.

5. The apparatus of claim 4, wherein the tube has a length of 1 to 4 feet.

6. The apparatus of claim 5, wherein the tube has a length of approximately 2 feet.

7. The apparatus of claim 1, wherein the tube is cylindrical.

8. The apparatus of claim 1, wherein the inner diameter of the tube is 0.1 to 4 inches.

9. The apparatus of claim 8, wherein the inner diameter of the tube is 0.25 to 1 inch.

10. The apparatus of claim 9, wherein the inner diameter of the tube is approximately 0.5 inches.

11. A system for transforming a wide-angle light source into a spot lighting source for observing the fire of gemstone, comprising:
    a wide-angle white light source;
    a hollow tube having an inlet and an outlet, positioned such that a portion of light from the light source is received at the inlet, channeled through the tube, and provided from the outlet as spot lighting to the gemstone, the spot lighting having approximately the same spectrum as the light from the light source;
    a mask to shield the gemstone from light generated from the wide angle light source, other than the channeled light portion; and
    a tray for supporting the gemstone.

12. The system of claim 11, wherein the white light source is a daylight-approximating halogen lamp.

13. The system of claim 11, wherein the tray is non-reflective.

14. The system of claim 11, wherein the tube is approximately 2 feet in length.

15. The system of claim 11, wherein an inner diameter of the tube is approximately 0.5 inches.

16. The system of claim 11, further comprising a mounting mechanism, coupled to the tube between the first and second ends, for mounting and aligning the tube inlet near the light source.

17. The system of claim 11, wherein the mask is a disk and is horizontally coupled with the tube.

18. A method of transforming a wide angle white light source into a spot lighting source for observing the fire of a gemstone, comprising:
   receiving a portion of light from the wide angle white light source at an inlet of a hollow tube;
   channeling the received portion of light through the tube;
   shielding light generated from the wide angle light source, other than the channeled light portion, from illuminating the gemstone; and
   outputting the channeled light as spot lighting from an outlet of the hollow tube, wherein the spot lighting has approximately the same spectrum as the light from the white light source.

19. The method of claim 18, further comprising positioning the inlet in an alignment with the light source.

* * * * *